United States Patent
Bellaton et al.

(10) Patent No.: US 10,132,830 B2
(45) Date of Patent: Nov. 20, 2018

(54) METHOD OF MEASURING A TOPOGRAPHIC PROFILE AND/OR A TOPOGRAPHIC IMAGE

(71) Applicant: Anton Paar TriTec SA, Peseux (CH)

(72) Inventors: Bertrand Bellaton, Neuchâtel (CH); Richard Consiglio, Neuchâtel (CH); Jacques Woirgard, La Grimaudière (FR)

(73) Assignee: Anton Paar TriTec SA, Peseux (CH)

( * ) Notice: Subject to any disclaimer, the term of this patent is extended or adjusted under 35 U.S.C. 154(b) by 339 days.

(21) Appl. No.: 15/001,049

(22) Filed: Jan. 19, 2016

(65) Prior Publication Data

US 2017/0138982 A1    May 18, 2017

(30) Foreign Application Priority Data

Nov. 18, 2015    (CH) ...................................... 1679/15

(51) Int. Cl.
| | |
|---|---|
| *G01Q 20/00* | (2010.01) |
| *G01Q 30/02* | (2010.01) |
| *G01N 3/42* | (2006.01) |
| *G01Q 60/38* | (2010.01) |

(52) U.S. Cl.
CPC ............ *G01Q 20/00* (2013.01); *G01N 3/42* (2013.01); *G01Q 30/02* (2013.01); *G01Q 60/38* (2013.01)

(58) Field of Classification Search
CPC ........ G01Q 20/00; G01Q 30/02; G01Q 60/38; G01N 3/42
USPC ...................................................... 73/862.01
See application file for complete search history.

(56) References Cited

U.S. PATENT DOCUMENTS

| | | | |
|---|---|---|---|
| 4,852,397 A * | 8/1989 | Haggag .................... | G01N 3/42 73/82 |
| 6,718,820 B2 * | 4/2004 | Kwon ...................... | G01N 3/48 73/81 |
| 7,568,381 B2 | 8/2009 | Smith | |
| 7,685,868 B2 * | 3/2010 | Woirgard ................ | G01N 3/42 73/81 |

(Continued)

FOREIGN PATENT DOCUMENTS

| | | |
|---|---|---|
| EP | 1 828 744 A1 | 9/2007 |
| EP | 2 816 342 A1 | 12/2014 |

*Primary Examiner* — Lisa Caputo
*Assistant Examiner* — Nathaniel T Woodward
(74) *Attorney, Agent, or Firm* — Christensen O'Connor Johnson Kindness PLLC

(57) ABSTRACT

Measuring a topographic profile and/or a topographic image of a surface of a sample includes positioning an indenter out of contact with a sample and in a constant position with respect to a headstock; positioning a topographic tip to detect a surface of the sample and positioning a reference structure at a predetermined distance from said surface; measuring the relative position of the indenter with respect to the reference structure by a relative position sensor; translating said sample perpendicular to said longitudinal axis while maintaining the reference structure at said predetermined distance from the surface of the sample by the feedback control system and the second actuator while measuring the relative position of the indenter with respect to the reference structure by the relative position sensor; and generating a topographic profile and/or a topographic image based on measurements of the relative position.

8 Claims, 3 Drawing Sheets

(56) References Cited

U.S. PATENT DOCUMENTS

| | | | | |
|---|---|---|---|---|
| 8,117,892 B2* | 2/2012 | Kawazoe | ................ | G01N 3/42 |
| | | | | 702/94 |
| 2003/0070475 A1* | 4/2003 | Nagashima | .............. | G01N 3/42 |
| | | | | 73/81 |
| 2008/0028840 A1* | 2/2008 | Smith | ...................... | G01N 3/42 |
| | | | | 73/81 |
| 2010/0088788 A1* | 4/2010 | Chasiotis | ............... | G01N 19/04 |
| | | | | 850/33 |

* cited by examiner

METHOD OF MEASURING A TOPOGRAPHIC PROFILE AND/OR A TOPOGRAPHIC IMAGE

TECHNICAL FIELD

The present invention relates to the field of material measurements. More particularly, it relates to a method of making a topographic measurement of an indentation test by using an indentation instrument comprising a topographic tip.

BACKGROUND

Atomic force microscopy (AFM) and other types of small-scale microscopy are well-known for taking topographical measurements of the profile of surfaces, with measurements often down to the nanometer scale. Such measurements are often used in combination with indentation testing machines to generate a profile of the indentation after it has been made, so as to generate useful data about the residual profile of the indentation. This is particularly useful in the case of scratch tests, in which an indenter is dragged across a sample surface under a constant or varying indentation force. As a result, two-dimensional data relating to the residual indentation depth can be generated, and by scanning in multiple parallel passes, three-dimensional data relating to the test can be generated.

Typically, an AFM may be provided as a bolt-on supplementary module for an indentation test apparatus, which puts a large distance between the indenter and the tip, thereby requiring large displacements of the sample so as to make a topographic measurement. However, several prior art indentation testers integrate an AFM (or similar) tip with the indenter, which serves to position the indenter and is used for measuring penetration depth, reducing this distance and thus enabling more precise referencing of the topographic measurement. For instance, U.S. Pat. No. 7,568,381 describes use of an AFM tip as part of a reference sensor, as does EP 2 816 342.

Typically, using the AFM tip to take a topographic measurement requires typical dedicated AFM sensors to be incorporated in the apparatus to make measurements with the AFM tip rather than just to detect the surface of the sample, which adds complexity and cost.

An aim of the present invention is thus to propose a method for taking topographic measurements of the surface of a sample using an indentation apparatus without having to provide further sensors other than those already provided on the indentation apparatus.

SUMMARY

This aim is achieved by a method of measuring a topographic image and/or a topographic profile of a surface of a sample according to claim 1. This method is described in the following paragraphs.

Firstly, an indentation instrument is provided, which comprises a headstock, an indenter mounted on said headstock by means of (i.e. indirectly via) a first actuator arranged to displace the indenter parallel to a longitudinal axis of the indenter, and a force sensor adapted to measure a force applied by said indenter. The indentation instrument also comprises a reference structure mounted on said headstock by means of (i.e. indirectly via) a second actuator arranged to displace the reference structure parallel to said longitudinal axis, a topographic tip mounted on said reference structure and adapted to detect a surface of a sample, for instance by determining a predetermined interaction between the topographic tip and the sample as described in more detail below, and a relative position sensor adapted to determine a relative position of the indenter with respect to the reference structure. A feedback control system is provided, which is adapted to control the second actuator based on detection of a surface of a sample by the topographic tip, as is a sample holder arranged to hold the sample facing the indenter and the topographic tip, the sample holder being arranged to be displaced in at least one direction perpendicular to said longitudinal axis. The sample holder typically comprises a positional readout as is generally known.

A sample is provided on the sample holder, and the indenter is positioned out of contact with said sample and in a constant position with respect to the headstock.

Subsequently, the topographic tip is positioned so as to detect the surface of the sample and the reference structure is thereby positioned at a predetermined distance from the said surface as detected by the topographic tip (i.e. the part of the surface detected by the tip) by means of the feedback control system and the second actuator.

The relative position of the indenter is then measured with respect to the reference structure by means of the relative position sensor, i.e. by means of measuring and recording the relative position of the reference structure with respect to the indenter, this latter being in a fixed vertical position with respect to the headstock, and the sample is then moved in translation perpendicular to said longitudinal axis while maintaining the reference structure at said predetermined distance from the surface of the sample as detected by the topographic tip by means of the feedback control system and the second actuator while measuring the relative position of the indenter with respect to the reference structure by means of the relative position sensor. The topographic tip is thus caused to maintain constant interaction with the surface of the substrate by the feedback control system and the actuator, and hence the reference structure correspondingly tracks up and down to follow the surface. The resulting vertical displacement of the reference structure with respect to the fixed vertical position of the indenter is thus measured by the relative position sensor, whose output is then used to generating a topographic image and/or a topographic profile based on measurements of the relative position of the indenter with respect to the reference structure. The terms "topographic profile" pertain to a cross sectional view along a line drawn through a portion of a surface topography map and the terms "topographic image" pertain to a surface topography map. Hence, the topographic profile is two-dimensional and based on a single pass of the topographic tip and the topographic image is three-dimensional and reconstructed from multiple parallel passes of the topographic tip, i.e. reconstructed from multiple topographic images.

Advantageously, prior to the step of positioning the indenter out of contact with the sample, an indentation test is carried out by means of the indenter. This indentation test may be a simple indentation test, or a scratch test in which the sample is moved perpendicular to the longitudinal axis of the indenter during the indentation, as is generally known.

The constant position of the indenter parallel to said longitudinal axis may be verified by means of said force sensor, which may comprise a spring disposed between the indenter and the actuator, the relative displacement detector being arranged to detect a relative displacement between said indenter and a structure mounted between the spring and said first actuator, said relative displacement detector comprising a differential capacitor comprising a first pair of electrodes provided on said structure, each of said electrodes facing a corresponding electrode of a second pair of electrodes provided on said indenter. A simple way to determine that the indenter is out of contact with the surface and in a constant position is by measuring a zero force by means of said force sensor, and maintaining the first actuator in a fixed position or state.

Advantageously, the relative position sensor comprises a further differential capacitor comprising a further first pair of electrodes provided on said reference structure, each of said electrodes facing a corresponding electrode of a further second pair of electrodes provided on said indenter. This can be the case irrespective of the nature of the force sensor, i.e. whether this latter also uses a differential capacitor or not.

Finally, the invention also relates to a product, comprising a computer-readable medium, and a computer program product comprising computer-executable instructions on the computer-readable medium for causing an indentation instrument of the type defined above to carry out the method as defined above.

BRIEF DESCRIPTION OF THE DRAWINGS

Further details of the invention will appear more clearly upon reading the following description in reference to the appended figures, which show.

DETAILED DESCRIPTION

Figure 1:
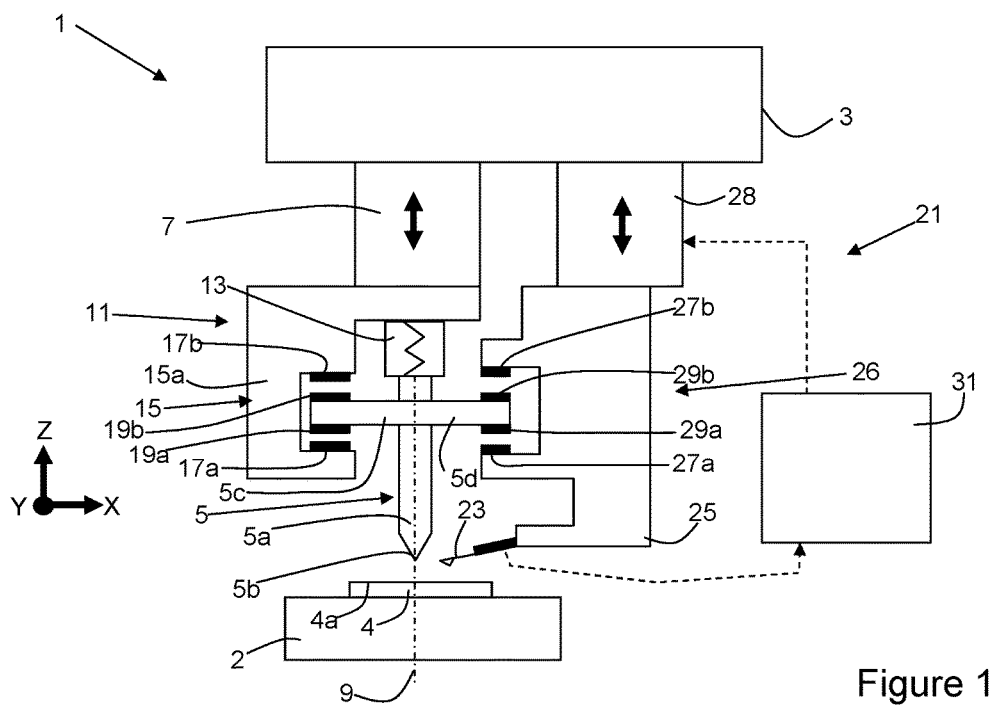
FIG. 1 an indentation instrument with which the method of the invention is carried out.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof.

Thus, the scope of the expression "a device comprising means A and B" should not be limited to devices consisting only of components A and B. It means that with respect to the present invention, the only relevant components of the device are A and B.

FIG. 1 illustrates an indentation instrument 1 as described in EP 2 816 342, herein incorporated by reference in its entirety. This indentation instrument comprises a headstock 3 upon which is mounted an indenter 5 by means of a first actuator 7. First actuator 7 may be a piezoelectric actuator or any other convenient type capable of applying sufficient force for the desired indentation applications.

As illustrated, indenter 5 comprises an indenter rod 5a extending along a longitudinal axis 9 parallel to the Z axis as indicated on the figure, and terminating at its distal end with an indentation tip 5b. This tip may be of hardened steel, tungsten, diamond, corundum, sapphire or similar, as is generally known. In the case of a metal tip, the tip 5b may be formed integrally with the intender rod 5a. Furthermore, the rod 5a comprises a laterally-extending flange 5c, the function of which will appear more clearly below. A sample holder 2 is adapted to support a sample 4 facing the tip 5b of the indenter 5, and is typically motorised and adapted to be moved along at least three axes X, Y and Z, and may also rotate about one or more of these axes, with accurate position detection. The position of the sample holder in at least the X and Y directions, and ideally also the Z direction, is determined by sensors so as to give a positional readout as is generally known.

The proximal end of the rod 5a is attached to the first actuator 7 by means of a force sensor 11. Force sensor 11 comprises a calibrated spring 13 of known spring constant k which is arranged so as to force the indenter 5 away from the actuator, and a relative displacement detector 15. Relative displacement detector 15 comprises a structure 15a mounted between the spring 13 and the first actuator 7, the structure 15a extending parallel to the indenter rod 5a and being provided with a first pair of electrodes 17a, 17b facing a corresponding second pair of electrodes 19a, 19b situated on the flange 5c of the indenter 5 so as to form a differential capacitor formed of a first capacitor 17a, 19a and a second capacitor 17b, 19b. As illustrated, the flange 5c extends towards the structure 15a into an interstice formed between the electrodes 17a, 17b so as to position electrodes 19a, 19b there between and extend substantially perpendicularly to longitudinal axis 9, although other configurations are possible such as the inverse construction in which electrodes 19a, 19b are each provided on a different flange facing each other, electrodes 17a, 17b being situated on either side of a protrusion provided on the structure 15a extending in the direction of the indenter 5, again extending perpendicularly to longitudinal axis 9.

Electrodes 17a, 17b, 19a, 19b are electrically connected to appropriate measurement and recording circuitry (not illustrated), and by measuring the difference in capacitance between first capacitor 17a, 19a and second capacitor 17b, 19b, the relative position of the indenter 5 and the structure 15a can be determined by any known method. This result, combined with knowing spring constant k of spring 13, permits determining the force applied by the indenter 5 on the sample 4. This principle is explained at length in document EP 1 828 744, herein incorporated by reference in its entirety, and thus need not be explained further here.

However, in the context of the present invention, other types of force sensor can be used, such as direct piezoelectric measurement of the force applied, separate to the first actuator 7 or combined therewith.

In order to measure the penetration depth of the indenter with respect to the sample 4 during an indentation measurement, the indentation instrument 1 also comprises a measurement subsystem 21 for measuring the penetration depth. This subsystem 21 comprises a topographic tip 23, arranged to detect the surface 4a of the sample 4. As illustrated, topographic tip 23 is a cantilevered atomic force microscope (AFM) probe, however other types of probes common for scanning probe microscopy in general are also possible. Self-evidently, the form of the tip should be sufficiently small and appropriately shaped for the desired measurement resolution. By "detect" the surface 4a of the sample, not only are contact-based detections such as those based on optical detection of a predetermined deflection of the probe meant, but also non-contact detections such as by using a vibrating AFM probe and detecting a predetermined change in amplitude, phase or frequency of the vibration caused by Van der Waals interactions between the atoms of the surface 4a of the sample 4 and the tip of the probe.

Topographic tip 23 is mounted on a reference structure 25, which is itself mounted on a second actuator 28 which may be of similar nature to first actuator 7, and serves to displace the reference structure 25 and hence the topographic tip 23 parallel to the Z axis. Driving and/or measuring systems required for the topographic tip 23 (not illustrated) to detect the surface 4a of the sample 4 may also be provided on or in reference structure 25. Such driving and/or measuring systems may for instance vibrate the tip, measure its vibrations, detect optically or (piezo-) electrically movement of the tip, and so on. Such systems are known per se and thus do not need to be described further, and may for instance "detect" the surface by determining a predetermined deflection of an AFM cantilever, a predetermined change in amplitude, phase or frequency of a vibrating AFM tip, or a predetermined force applied to the surface.

Reference structure 25 also comprises a relative position sensor 26. In the present example, this comprises a further first pair of electrodes 27a, 27b forming a further differential capacitor in combination with corresponding further second pair of electrodes 29a, 29b provided on a further laterally-extending flange 5d of the indenter rod 5, which may be integral with the flange 5c or separate therefrom. Electrodes 27a, 27b, 29a, 29b again extend substantially perpendicular to longitudinal axis 9. These capacitors 27a, 29a and 27b, 29b are constructed similarly to capacitors 17a, 19a and 17a, 19b, and all comments in respect of these latter capacitors apply equally to the former, mutatis mutandis. Hence, again by comparing the difference in capacitance between capacitors 27a, 29a and 27b, 29b by any convenient method, the relative position of the indenter 5 and the reference structure 25 can be determined. Other forms of relative position sensor 26 arranged to measure the relative position of the indenter 5 with respect to the reference structure 25 (such as optical-based systems) are also possible.

Furthermore, the indentation instrument 1 comprises a feedback control system 31 which is in operative connection with the topographic tip 23 and the second actuator 28, so as to drive the second actuator 28 so as to adjust the position of the reference structure with respect to the sample 4 as will be described below in the context of FIG. 2.

Figure 2:
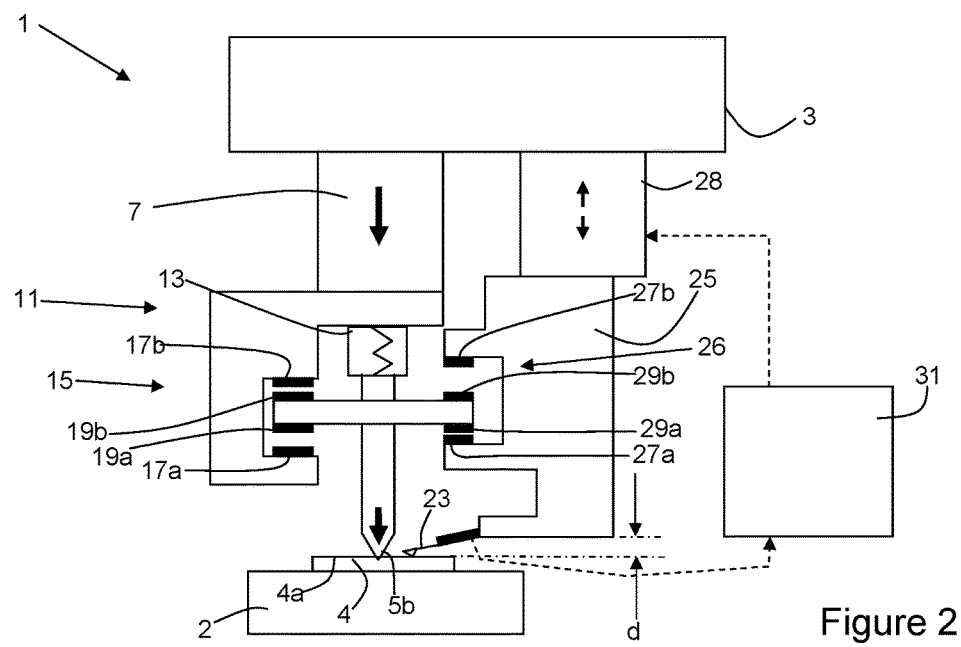
FIG. 2 the indentation instrument of FIG. 1, shown carrying out an indentation operation.
Figure 3:
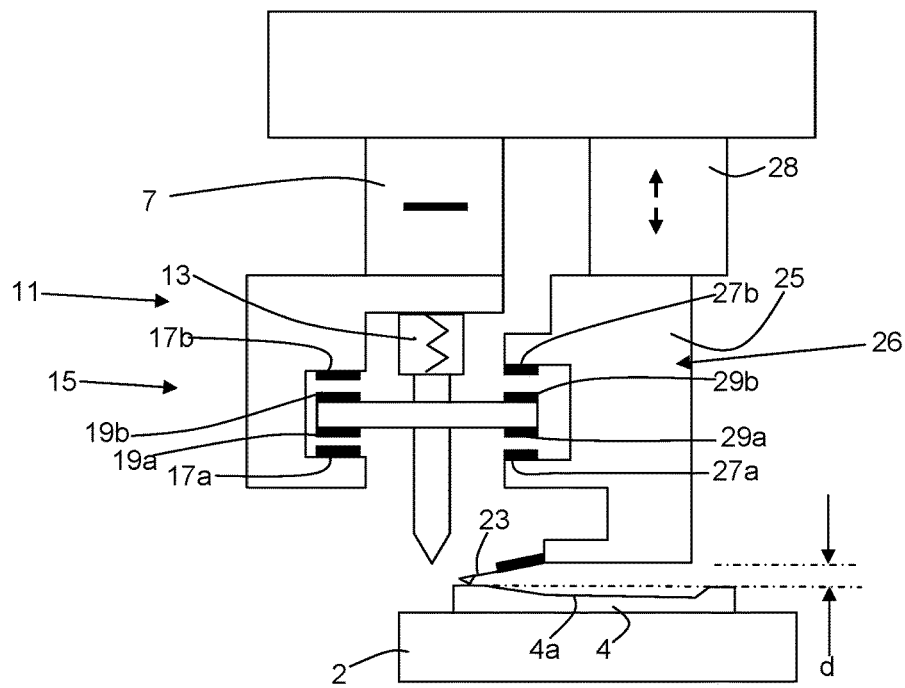
FIG. 3-6 the indentation instrument of FIG. 1, shown at various stages of making a topographic measurement of a scratch test.

FIG. 2 illustrates the position of the various components of the indentation instrument 1 during an indentation test. In FIG. 2 and subsequent figures, only reference signs referred to in the text are reproduced in order to avoid cluttering the figures, and vertical displacements have been exaggerated for clarity. Furthermore, the feedback control system 31 has not been illustrated from FIG. 3 onwards.

In FIG. 2, the indenter tip 5b has penetrated into the surface 4a of the sample 4 under a force applied by first actuator 7 and measured by force sensor 11. Before the indentation takes place, however, the sample is positioned close to the tip 5b of the indenter 5 and to the topographic tip 23 by means of displacing the sample holder 2, and/or displacing the headstock 3, and/or moving the indenter 5 and topographic tip 23 in the Z direction by means of first actuator 7 and second actuator 28 respectively, and the reference structure is then positioned at a predetermined distance d from the surface 4a of the sample by actuating the second actuator 28 to move the reference structure 25 towards the surface 4a of the sample until the surface 4a thereof is detected by the topographic tip. Once the surface 4a has been detected, feedback control system 31 maintains the reference structure 25 at predetermined distance d by controlling second actuator 28 to make any required adjustments according to the Z axis so as to maintain the reference structure 25 in the desired vertical relation with the surface 4a. These adjustments are typically minuscule.

While the feedback control system 31 maintains the reference structure at a constant distance d, indenter tip 5b is brought into contact with the surface 4a of the sample 4 and is forced to penetrate into the surface 4a under a load applied by first actuator 7.

Since the reference structure 25 maintains a constant separation d from the surface 4a of the sample 4, the indenter 5 displaces towards the sample along the Z axis (i.e. downwards as illustrated in the figure) with respect to the reference structure 25, as clearly shown in FIG. 2. This causes the electrode 29a to approach electrode 27a, and electrode 29b to withdraw from electrode 27b, thereby changing the relative capacitance of the two capacitors 27a, 29a and 27b, 29b, from which the displacement of the indenter 5 with respect to the reference structure 25 can be calculated. These capacitors 27a, 29a; 27b, 29b are electrically connected (not shown) to suitable processing and recording circuitry. By incorporating the dimensions of the various components into the calculation, and/or by determining the point of contact between the indenter tip 5b and the sample based on output of the force sensor 11, the absolute penetration of the indenter tip 5b into the surface 4a of the sample 4 can be determined.

The force applied by the indenter 5 to the sample 4 is measured continuously by the force sensor 11, and can be correlated with that of the penetration depth of the indenter tip into the surface 4a of the sample 4. In the illustrated embodiment, since a force is applied between the surface 4a of the sample 4 and the indenter tip 5a, spring 13 is compressed, and the structure 15a moves downwards (towards the sample 4) with respect to the indenter rod 5a, causing electrodes 17b and 19b to approach each other, and electrodes 17a and 19a to withdraw from each other. The changes in capacitance thereby engendered can be used to determine the relative displacement of the indenter 5 with respect to the structure 15a and hence the force applied at any moment.

This system can not only perform a static indentation test under a static or dynamic load, but also by displacing the sample 4 laterally during indentation, scratch tests can be carried out, again under static or dynamic indentation loads.

Traditionally, in order to make topographic measurements of an indentation created by the indenter 5 or simply to measure any surface profile desired, a separate topographic measurement module (typically an AFM module) is provided off to the side of the indenter. However, this results in a significant distance being present between the measurement tip of the measurement module, resulting in large movements of the sample or the headstock to bring it into action and take a measurement. This limits the precision of placement of the measurement tip on the indentation.

One particular solution to this problem would be to provide a full suite of conventional topographic measurement elements and systems associated with the topographic tip 23 integrated with the reference structure 25. As a result, once the indentation has been made, the indenter 5 can be withdrawn and the topographic tip can be operated conventionally, the dedicated conventional measurement elements and systems performing this measurement in the conventional fashion. This is the solution implied in EP 2 816 342.

However, such a solution requires integration of the aforementioned full suite of conventional measurement elements, which is costly and significantly complicates construction of the indentation system 1.

The method of the present invention obviates the need to incorporate such conventional topographic measurement elements by using the existing sensors present in the indentation system 1 to carry out not only the measurement of the indentation depth as described above, but also the topographic measurement in addition. It should be noted that the method can also be used for making a topographic measurement of any substantially planar sample 4, whether indented or not.

This method is illustrated in FIGS. 3-6, in the context of taking a topographic measurement of a scratch test previously carried out on the same indentation apparatus 1, however applies equally to any other sample 4 for which a topographic measurement is required.

Figure 4:
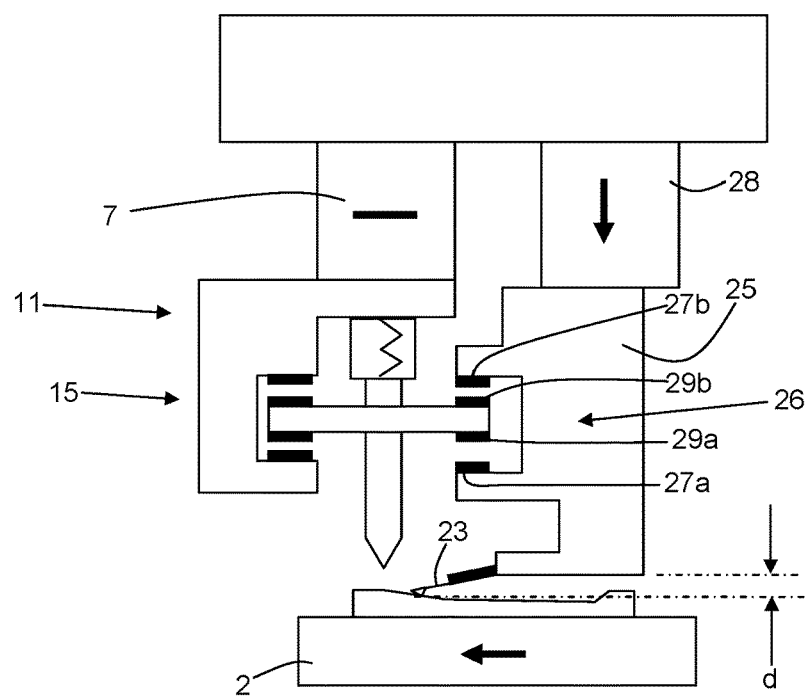
Figure 5:
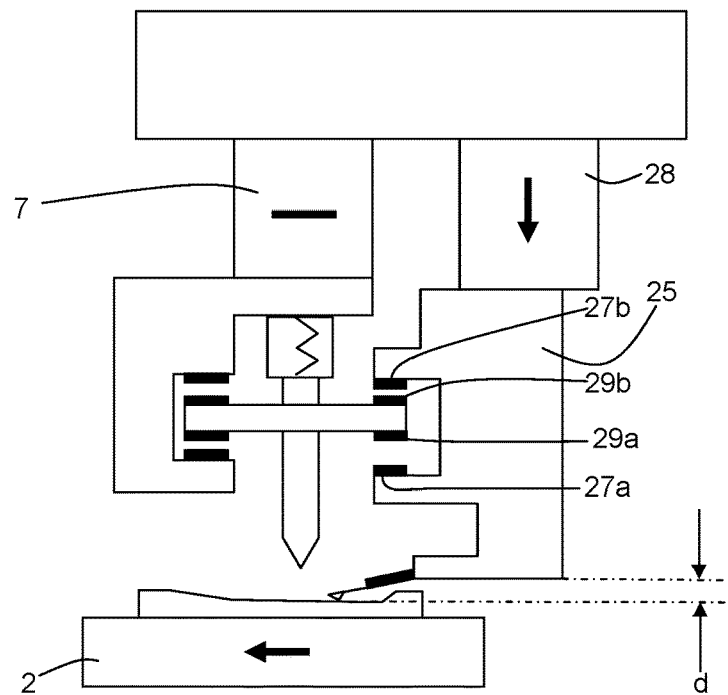
Figure 6:
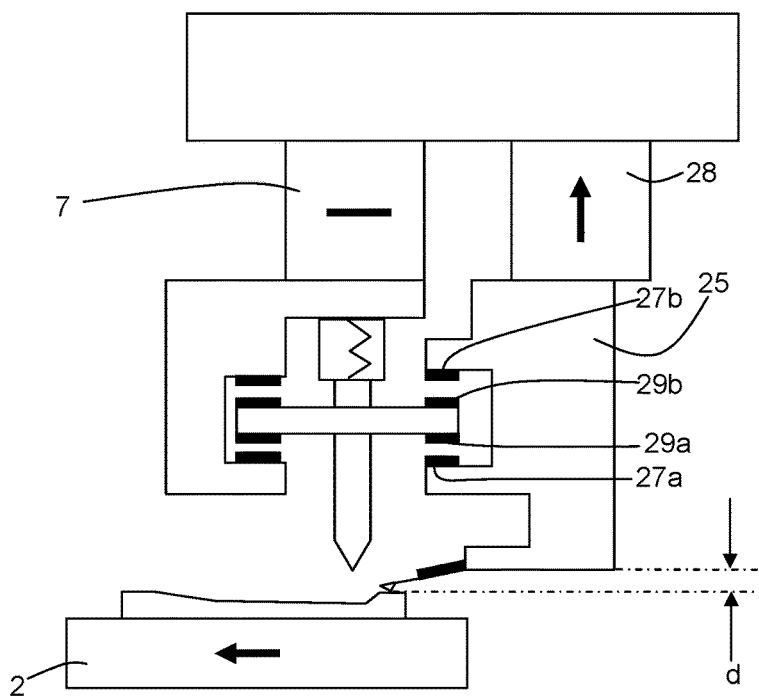

As can be seen in FIGS. 4-6, the indentation instrument 1 and the sample 4 have been provided. The surface 4a of the sample 4 is depressed following the track of a previously-performed scratch test, the sectional view of the figures being taken along the centreline of the scratch test which deepens from left to right.

Firstly, the indenter tip 5b is positioned out of contact with the sample 4 by the actuator. The indenter tip 5b remains out of contact with the surface 4a of the sample 4 throughout the measurement. Since there is no force acting on the tip 5b, the spring 13 causes the indenter 5 to adopt a neutral position, which can be verified by the capacitors 17a, 19a and 17b, 19b if required, by checking that the force measured by the force sensor 11 is zero. If required, this verification can be carried out continuously throughout a topographic measurement. In its simplest form, the first actuator 7 can simply be driven into an arbitrary position and deactivated, or can be placed in an extreme position (such as to position the indenter 5 as close to the headstock 3 as possible, or as far away from the headstock 3 as possible) against a mechanical stop (not illustrated). In the case of another type of force sensor such as a piezoelectric force sensor, the same comments regarding the first actuator 7 apply equally. Indenter 5 thus maintains a constant vertical (Z-axis) position with respect to the headstock 3 and to the sample 4, and serves as a Z-axis reference.

Topographic tip 23 is then placed so as to detect the surface 4a of the sample 4 at a desired start point of the topographic measurement as described above in the context of making an indentation measurement. A convenient start point of the measurement is immediately adjacent to the scratch test. Control system 31 (not illustrated on FIGS. 3-6 to avoid cluttering the figures) again positions the reference structure 25 at predetermined distance d from the surface 4a of the sample 4 as detected by the topographic tip 23. The relative position between the indenter 5 and the reference structure is then determined by the relative position sensor 26, and can be taken as a datum point for taking the topographic measurement.

Subsequently, the substrate 4 is moved laterally with respect to the topographic tip 23, i.e. perpendicular to axis Z, by means of translating the sample holder 2 with respect to the headstock 3 or vice-versa. In the example of the figures, the sample holder is moved to the left so as to scan the topographic tip towards the right along the scratch test in the surface 4a of the substrate 4.

In FIG. 4, the sample 4 has been translated leftwards, and the topographic tip has descended into the scratch test present in the surface 4a. This is carried out by the feedback control system commanding the second actuator to maintain the predetermined distance d between the reference structure 25 and the surface 4a of the sample as detected by the topographic tip 23 as the sample is translated. Since the surface profile deepens as the sample 4 moves leftwards, the actuator drives the reference structure downwards in the direction of the substrate so as to follow the surface. Reference structure 25 thus descends with respect to the intender 5, which has remained in the same vertical position as a reference, electrodes 27b, 29b have approached each other, and electrodes 27a, 29a have separated. The resulting change in capacitance is used to determine the new relative position of the reference structure 25 with respect to the indenter 5, which thus generates the topographic measurement by taking multiple measurements along the sample. In essence, the indenter 5 having been placed in an unchanging vertical position with respect to not only the headstock 1 but also with respect to the sample holder, which is only translated perpendicular to the axis Z, it serves as a fixed vertical reference, against which the vertical position of the reference structure 25 is compared throughout the topographic measurement. The topographic measurement is thus carried out by measuring vertical movements of the reference structure 25 and topographic tip 23 with reference to the indenter 5.

As the sample 4 continues to translate to the left (FIGS. 4 and 5), the surface 4a indentation profile deepens, and the reference structure 25 is driven further downwards to maintain predetermined distance d and thus to follow the surface. Indenter 5 maintains its vertical position with respect to the headstock 3, and hence electrodes 27b, 29b further approach each other, and electrodes 27a, 29a further separate from one another.

In FIG. 5, the sample 4 continues translating leftwards and the topographic tip 3 has left the depression left in the surface 4a by the scratch test. The control system 31 always driving the second actuator 28 to maintain the distance d, it has driven the reference structure upwards towards the headstock 3, and hence electrodes 27b, 29b have separated, and electrodes 27a, 29a have returned towards each other.

By measuring the changes in capacitance of capacitors 27a, 28a and 27b, 28b, calculating the corresponding relative displacements between the reference structure 25 and the indenter 5, and correlating these relative displacements with measurements of the translation of the sample 4, the topographic profile of the scratch test can be measured. By displacing the sample 4 a predetermined distance in the Y direction (into or out of the page) and repeating the process, thereby scanning the topographic tip 23 in several passes in a grid or raster pattern, three-dimensional topographic profiles can be measured and images created.

The principle of the method also applies equally for any other form of non-capacitive relative position sensor 26.

Although this method has been described in terms of a scratch test, any suitable surface can be measured by the same process.

The above-mentioned method can be carried out under computer control by following instructions contained in a computer program product stored on a computer-readable medium (CD-ROM, DVD, hard disk, flash drive etc.).

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A method of measuring one or both of a topographic image or a topographic profile of a surface of a sample, the method comprising:
   (a) providing an indentation instrument comprising:
      a headstock,
      an indenter mounted on said headstock by a first actuator configured to displace the indenter parallel to a longitudinal axis of the indenter,
      a force sensor configured to measure a force applied by said indenter,
      a reference structure mounted on said headstock by a second actuator configured to displace the reference structure parallel to said longitudinal axis,
      a topographic tip mounted on said reference structure and configured to detect a surface of a sample,
      a relative position sensor configured to determine a relative position of the indenter with respect to the reference structure,
      a feedback control system configured to control the second actuator based on detection of said surface of said sample by the topographic tip, and
      a sample holder configured to hold said sample facing the indenter and the topographic tip, the sample holder being configured to be displaced in at least one direction perpendicular to said longitudinal axis;
   (b) providing the sample on the sample holder;
   (c) positioning the indenter out of contact with said sample and in a constant position with respect to the headstock;
   (d) positioning the topographic tip so as to detect the surface of the sample and positioning the reference structure at a predetermined non-zero distance from said surface as detected by the topographic tip by the feedback control system and the second actuator;
   (e) measuring the relative position of the indenter with respect to the reference structure by the relative position sensor;
   (f) translating said sample perpendicular to said longitudinal axis while maintaining the reference structure at said predetermined non-zero distance from the surface of the sample, as detected by the topographic tip, by the feedback control system and the second actuator while measuring the relative position of the indenter with respect to the reference structure by the relative position sensor; and
   (g) generating one or both of a topographic profile or a topographic image based on measurements of the relative position of the indenter with respect to the reference structure.

2. A method according to claim 1, further comprising, before step (c), a step of:
   carrying out an indentation test on said sample by said indenter.

3. A method according to claim 2, wherein said indentation test is a scratch test.

4. A method according to claim 1, wherein the constant position of the indenter parallel to said longitudinal axis is verified by said force sensor.

5. A method according to claim 4, wherein said constant position is determined by measuring a zero force by said force sensor while maintaining the first actuator in a fixed position.

6. A method according to claim 1, wherein said force sensor comprises a spring disposed between the indenter and the first actuator, a relative displacement detector being configured to detect a relative displacement between said indenter and a structure mounted between the spring and said first actuator, said relative displacement detector comprising a differential capacitor comprising a first pair of electrodes provided on said structure, each of said electrodes facing a corresponding electrode of a second pair of electrodes provided on said indenter.

7. A method according to claim 1, wherein the relative position sensor comprises a further differential capacitor comprising a further first pair of electrodes provided on said reference structure, each of said electrodes facing a corresponding electrode of a further second pair of electrodes provided on said indenter.

8. A non-transitory computer-readable medium having computer-executable instructions on the non-transitory computer-readable medium for measuring one or both of a topographic image or a topographic profile of a surface of a sample using an indentation instrument, wherein:
   said indentation instrument comprises:
      a headstock,
      an indenter mounted on said headstock by a first actuator configured to displace the indenter parallel to a longitudinal axis of the indenter,
      a force sensor configured to measure a force applied by said indenter,
      a reference structure mounted on said headstock by a second actuator configured to displace the reference structure parallel to said longitudinal axis,
      a topographic tip mounted on said reference structure and configured to detect a surface of a sample,
      a relative position sensor configured to determine a relative position of the indenter with respect to the reference structure,
      a feedback control system adapted to control the second actuator based on detection of said surface of said sample by the topographic tip, and
      a sample holder configured to hold said sample facing the indenter and the topographic tip, the sample holder being adapted to be displaced in at least one direction perpendicular to said longitudinal axis; and
   said instructions, in response to execution by one or more computing devices, cause the indentation instrument to:
      position the indenter out of contact with said sample and in a constant position with respect to the headstock,
      position the topographic tip so as to detect the surface of the sample and positioning the reference structure at a predetermined non-zero distance from said surface as detected by the topographic tip by the feedback control system and the second actuator,
measure the relative position of the indenter with respect to the reference structure by the relative position sensor,
translate said sample perpendicular to said longitudinal axis while maintaining the reference structure at said predetermined non-zero distance from the surface of the sample, as detected by the topographic tip, by the feedback control system and the second actuator while measuring the relative position of the indenter with respect to the reference structure by the relative position sensor, and
generate one or both of a topographic profile or a topographic image based on measurements of the relative position of the indenter with respect to the reference structure.

\* \* \* \* \*